United States Patent
Fukuhara et al.

(10) Patent No.: US 7,829,741 B2
(45) Date of Patent: Nov. 9, 2010

(54) PROCESS FOR PRODUCING α, α-DIFLUOROAMINE

(75) Inventors: Tsuyoshi Fukuhara, Hokkaido (JP); Shoji Hara, Hokkaido (JP); Toshio Hidaka, Ibaraki (JP)

(73) Assignees: National University Corporation, Hokkaido (JP); Mitsubishi Gas Chemical Company, Inc., Tokyo (JP)

( * ) Notice: Subject to any disclaimer, the term of this patent is extended or adjusted under 35 U.S.C. 154(b) by 200 days.

(21) Appl. No.: 11/718,526

(22) PCT Filed: Oct. 20, 2005

(86) PCT No.: PCT/JP2005/019283

§ 371 (c)(1),
(2), (4) Date: Feb. 23, 2009

(87) PCT Pub. No.: WO2006/049014

PCT Pub. Date: May 11, 2006

(65) Prior Publication Data

US 2009/0177012 A1   Jul. 9, 2009

(30) Foreign Application Priority Data

Nov. 5, 2004  (JP) ............................ 2004-322987

(51) Int. Cl.
*C07C 209/68* (2006.01)
*C07C 209/74* (2006.01)

(52) U.S. Cl. ................... 564/412; 564/366; 564/496; 564/510

(58) Field of Classification Search ................ None
See application file for complete search history.

(56) References Cited

U.S. PATENT DOCUMENTS

| | | | |
|---|---|---|---|
| 5,336,809 A | | 8/1994 | Bohm et al. |
| 6,747,175 B2 * | | 6/2004 | Kempf et al. ............... 564/412 |
| 2005/0085474 A1 | | 4/2005 | Ebenbeck et al. |
| 2006/0014972 A1 | | 1/2006 | Hara et al. |

FOREIGN PATENT DOCUMENTS

| | | |
|---|---|---|
| EP | 0 895 991 | 2/1999 |
| JP | 06-009480 | 1/1994 |
| JP | 07-292490 | 11/1995 |
| JP | 11-049742 | 2/1999 |
| JP | 2000-001477 | 1/2000 |
| JP | 2003-064034 | 3/2003 |
| JP | 2004-231646 | 8/2004 |
| WO | WO 2004/050676 | 6/2004 |

OTHER PUBLICATIONS

Extended European Search Report, including Supplementary European Search Report and European Search Opinion, dated Mar. 2, 2010, for Application No. EP 05 79 5464.
L. M. Yagupolskii, et al., "N,N-Bis(difluoromethyl)anilines", *Journal of Fluorine Chemistry*, vol. 76, 1996, pp. 95-98.
Chinese Official Action issued May 8, 2009, for Application No. 200580037059.7 (English translation only).

* cited by examiner

*Primary Examiner*—Brian J Davis
(74) *Attorney, Agent, or Firm*—Antonelli, Terry, Stout & Kraus, LLP.

(57) ABSTRACT

A process for producing an α,α-difluoroamine which comprises using hydrogen fluoride and a Lewis base in specific amounts in the halogen-fluorine exchange reaction using an α,α-dihaloamine as the substrate. The process can be industrially applied, enables to obtain the object compound in a short time at a great yield and can be conducted easily with excellent productivity.

6 Claims, No Drawings

PROCESS FOR PRODUCING α,α-DIFLUOROAMINE

TECHNICAL FIELD

The present invention relates to a process for producing an α,α-difluoroamine which comprises using hydrogen fluoride and a Lewis base in specific amounts in the halogen-fluorine exchange reaction using an α,α-dihaloamine as the substrate, can be industrially applied, enables to obtain the object compound in a short time at a great yield and can be conducted easily with excellent productivity. The α,α-difluoroamine produced in accordance with the process of the present invention is used as the nucleophilic fluorinating agent useful for introducing fluorine into compounds for pharmaceutical applications, in particular.

BACKGROUND ART

As the typical process of fluorination for introducing fluorine atom into a substrate, heretofore, the direct fluorination using fluorine gas ($F_2$) has been known (for example, refer to Patent Reference 1). When the substrate has a functional group such as oxygen, sulfur and halogen, processes in which the functional group is replaced with fluorine atom using an inorganic fluorinating agent such as hydrogen fluoride (occasionally referred to as HF, hereinafter) and sulfur tetrafluoride or an fluorinating agent other than inorganic fluorinating agents such as pyridine-9HF (the Olah reagent), a Yarovenko reagent of the fluoro-alkylamine type, a modified Ishikawa reagent of the fluoro-alkylamine type or diethylamionosulfur trifluoride (DAST), have been known (for example, refer to Non-Patent References 1 and 3).

When the substrate is a halogen compound, the halogen-fluorine exchange reaction is the most convenient means for introducing fluorine. In the halogen-fluorine exchange, alkali metal salts of fluorine are used frequently. For example, sodium fluoride and potassium fluoride have little toxicity or possibility of causing corrosion unlike HF and can be handled easily. Potassium fluoride (occasionally referred to as KF, hereinafter) prepared in accordance with the spray drying process is frequently used recently (for example, refer to Non-Patent References 2 and 4).

As the agent other than those described above, molecular compounds of HF and a Lewis base such as pyridine or triethylamine, or ammonium fluoride salts can be used for the halogen-fluorine exchange reaction (for example, refer to Non-Patent References 3 and 4 (page 178)).

The processes for fluorination described above have a problem in that fluorine gas, hydrogen fluoride and sulfur tetrafluoride have toxicity and may cause corrosion and explosion, and special apparatuses and technologies are required for the handling.

To overcome the above problem and introduce fluorine safely and easily, various nucleophilic and electrophilic fluorinating agents have been developed (for example, refer to Patent References 2 and 3 and Non-Patent Reference 1). Patent Reference 3 relates to α,α-difluoro-amines proposed by the present inventors which are represented by the following general formula (1), can overcome the above problem of conventional processes, exhibit excellent heat stability and can be handled easily:

wherein $R_0$, $R_1$ and $R_2$ each represent hydrogen atom or an alkyl group, an aryl group, an alkylamino group or an arylamino group, which may have substituents, atoms and groups represented by $R_0$, $R_1$ and $R_2$ may be same with or different from each other, and a ring may be formed by bonding of two or more groups represented by $R_0$, $R_1$ and $R_2$.

The α,α-difluoroamine represented by general formula (1) can be produced in accordance with a conventional halogen-fluorine exchange reaction using as the precursor a halogen compound of an amide which is an α,α-dihaloamine represented by the following general formula (2):

wherein $R_0$, $R_1$ and $R_2$ each represent hydrogen atom or an alkyl group, an aryl group, an alkylamino group or an arylamino group, which may have substituents, atoms and groups represented by $R_0$, $R_1$ and $R_2$ may be same with or different from each other, a ring may be formed by bonding of two or more groups represented by $R_0$, $R_1$ and $R_2$, and X represents chlorine atom, bromine atom or iodine atom.

The α,α-difluoroamine represented by general formula (1) of the object compound can be obtained by the halogen-fluorine exchange reaction of the α,α-dihaloamine represented by general formula (2) using HF or an alkali metal salt of fluorine such as NaF and KF prepared in accordance with the spray drying process as the fluorine source.

The process for producing a fluorine compound by the fluorine exchange using HF or an alkali metal salt of fluorine such as NaF and KF has heretofore been known widely. The condition of the reaction can be decided with reference, for example, to Non-Patent Reference 3. However, occasionally, the reaction rate is insufficient, and it takes a long time to complete the reaction.

For example, when the reaction of N,N-diethyl-α-chlorometatoluoyl-amidium chloride is conducted using KF, which is prepared in accordance with the spray drying process, has a relatively great specific surface area and exhibits a great activity, in acetonitrile as the solvent under the refluxing condition (82° C.) for 24 hours, the yield is at most 70%. A long processing time not only lowers productivity of the object fluoroamines, but also results in an increased cost, and thus is a problem as an industrial process.

As described above, when an α,α-difluoroamine is produced in accordance with the halogen-fluorine exchange reaction using KF, the relatively great cost of KF prepared in accordance with the spray drying process and the long time required for the reaction are the major causes of the increase in the cost of production, and a further increase in the productivity and a further decrease in the cost are required from the standpoint of the industrial production.

Some of the above problems can be overcome by using a molecular compound of HF and a Lewis base (occasionally referred to as "HF-Lewis base", hereinafter) for the halogen-fluorine exchange reaction.

However, few examples of the application of HF-Lewis base to the production of the α,α-difluoroamine represented general formula (1) can be found. In particular, no references clearly describe that triethylamine-3HF comprising HF and triethylamine in relative amounts by mole of 3:1 (causing no corrosion and enabling to use a glass vessel; occasionally referred to as "Et$_3$N-3HF") exhibits a greater nucleophilicity than that of other HF-Lewis bases such as pyridine-9HF (the Olah reagent) and is advantageously used for the halogen-fluorine exchange reaction since the reaction is rapidly completed.

More specifically, in conventional processes, no examples can be found on the production of N,N-diethyl-α,α-difluoro (3-methyl)benzylamine using HF-Lewis base such as Et$_3$N-3HF in the chlorine-fluorine exchange reaction of N,N-diethyl-α-chlorometatoluoylamidium chloride. No examples can be found on the production of similar α,α-difluoroamines using HF-Lewis base, either.

When the use, for example, of Et$_3$N-3HF is applied to the production of α,α-difluoroamine, an unexpected difficulty arises as described in the following. When HF-Lewis base such as Et$_3$N-3HF is used for the halogen-fluorine exchange reaction, the ratio of the amounts by mole of HF and the Lewis base is not always 1:1, and HF derived from HF-Lewis base used for the reaction is left remaining after the halogen exchange reaction is completed. This causes a serious problem in that separation of the product becomes difficult since molecular compounds are formed due to the interaction between HF and the nitrogen atom in the substrate or the product. Moreover, there is the possibility that the remaining HF causes corrosion. The process becomes complicated since steps for separation and purification must be added for obtaining the product.

No patents or references which mention the problems described above such as the problems in the industrial production of α,α-difluoroamine using Et$_3$N-3HF or the means for solving the problems can be found.

[Patent Reference 1] Japanese Patent Application Publication No. Showa 63 (1988)-25570

[Patent Reference 2] Japanese Patent Application Laid-Open No. 2000-1477

[Patent Reference 2] Japanese Patent Application Laid-Open No. 2003-64034

[Non-Patent Reference 1] Yuki Gosei Kagaku Kyokaishi, 37, 1979, p. 606

[Non-Patent Reference 2] Yuki Gosei Kagaku Kyokaishi, 47, 1989, p. 258

[Non-Patent Reference 3] Journal of Organic Chemistry, 44, 1979, p. 3872

[Non-Patent Reference 4] Chemistry of Organic Fluorine Compounds II, Monograph, American Chem. Soc., 1995, p. 187

DISCLOSURE OF THE INVENTION

The present invention has an object of overcoming the above problems and providing a means which, in the production of an α,α-difluoroamine represented by general formula (1) in accordance with the halogen-fluorine exchange reaction using the α,α-dihaloamine represented by general formula (2) as the substrate, can prevent difficulties in obtaining the object product and in separation of the produced fluorine compound which are caused by the reaction of the substrate and/or the product molecule with the unreacted HF or HF-Lewis base due to the presence of nitrogen atom in the substrate and/or the product molecule, can rapidly complete the exchange reaction for which it has heretofore taken a long time, enables to easily separate and obtain the fluorine compound of the object compound and can be industrially applied with a great productivity.

As the result of intensive studies by the present inventors to achieve the above object, it was found that the object could be achieved by conducting the reaction using HF and a Lewis base in each specific amounts in the production of an α,α-difluoroamine. The present invention has been conducted based on this knowledge.

The present invention provides a process for producing an α,α-difluoroamine as described in the following.

[1] A process for producing an α,α-difluoroamine represented by general formula (1) in accordance with a halogen-fluorine exchange reaction using an α,α-dihaloamine represented by general formula (2) as a substrate, wherein hydrogen fluoride and a Lewis base are used for the exchange reaction each in an amount by mole in a range of 90 to 110% based on an amount by mole of a halogen atom represented by X in the α,α-dihaloamine, and a salt of a hydrogen halide and the Lewis base formed by the exchange reaction is removed to outside of a reaction system:

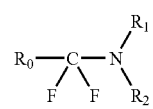

(1)

wherein R$_0$, R$_1$ and R$_2$ each represent hydrogen atom or an alkyl group, an aryl group, an alkylamino group or an arylamino group, which may have substituents, atoms and groups represented by R$_0$, R$_1$ and R$_2$ may be same with or different from each other, and a ring may be formed by bonding of two or more groups represented by R$_0$, R$_1$ and R$_2$;

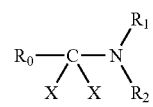

(2)

wherein R$_0$, R$_1$ and R$_2$ each represent hydrogen atom or an alkyl group, an aryl group, an alkylamino group or an arylamino group, which may have substituents, atoms and groups represented by R$_0$, R$_1$ and R$_2$ may be same with or different from each other, a ring may be formed by bonding of two or more groups represented by R$_0$, R$_1$ and R$_2$, and X represents chlorine atom, bromine atom or iodine atom.

[2] A process for producing an α,α-difluoroamine described in [1], wherein hydrogen fluoride and the Lewis base are introduced into the reaction system as a molecular compound of hydrogen fluoride and the Lewis base or a combination of the Lewis base and a molecular compound of hydrogen fluoride and the Lewis base.

[3] A process for producing an α,α-difluoroamine described in any one of [1] and

[2], wherein the Lewis base is triethylamine, n-butylamine, pyridine, quinoline, melamine, γ-cholidine, piperidine, piperazine or morpholine.

[4] A process for producing an α,α-difluoroamine described in [2], wherein the molecular compound of hydrogen fluoride and the Lewis base is triethylamine-3HF.

[5] A process for producing an α,α-difluoroamine described in any one of [1] to [4], wherein X in general formula (2) represents chlorine atom.

[6] A process for producing an α,α-difluoroamine described in any one of [1] to [5], wherein, in general formula (1) and general formula (2), $R_0$ represents phenyl group, 2-methylphenyl group, 3-methylphenyl group, 4-methylphenyl group, 4-ethylphenyl group, 4-n-propylphenyl group, 4-isopropylphenyl group, 4-n-butylphenyl group, 4-t-butylphenyl group, 4-isobutylphenyl group, 2-methoxyphenyl group, 3-methoxyphenyl group, 4-methoxyphenyl group, 2,4-dimethylphenyl group, 2,5-dimethylphenyl group, 3,4-dimethylphenyl group, 3,5-dimethylphenyl group, 2,4,5-trimethylphenyl group, 2,4,6-trimethylphenyl group, 4-methylbiphenyl group, 4-ethylbiphenyl group, 4-n-propylbiphenyl group or 4-n-butyl-biphenyl group, and $R_1$ and $R_2$ each represent an alkyl group or an aryl group each having 16 or less carbon atoms.

THE MOST PREFERRED EMBODIMENT TO CARRY OUT THE INVENTION

The present invention will be described more specifically in the following.

In the halogen-fluorine exchange reaction of the present invention, the α,α-dihaloamine represented by general formula (2) is used as the substrate.

As the α,α-dihaloamine, compounds represented by general formula (2) in which X represents chlorine, bromine or iodine are used. Among these halogen atoms, chlorine atom is preferable from the standpoint of the reactivity and the easiness of handling.

Preferable examples of the α,α-dihaloamine include compounds represented by general formula (2) in which $R_0$ represents phenyl group, 2-methylphenyl group, 3-methylphenyl group, 4-methylphenyl group, 4-ethylphenyl group, 4-n-propylphenyl group, 4-isopropylphenyl group, 4-n-butylphenyl group, 4-t-butylphenyl group, 4-isobutylphenyl group, 2-methoxyphenyl group, 3-methoxyphenyl group, 4-methoxyphenyl group, 2,4-dimethylphenyl group, 2,5-dimethylphenyl group, 3,4-dimethylphenyl group, 3,5-dimethylphenyl group, 2,4,5-trimethylphenyl group, 2,4,6-trimethylphenyl group, 4-methylbiphenyl group, 4-ethylbiphenyl group, 4-n-propylbiphenyl group or 4-n-butylbiphenyl group, and $R_1$ and $R_2$ each represent an alkyl group or an aryl group each having 16 or less carbon atoms.

The above α,α-dihaloamine can be derived from the corresponding amide, i.e., an amide having a structure in which the atoms represented by X in general formula (2) are replaced with oxygen atom. The above α,α-dihaloamine can be derived also from a compound analogous to the amide such as an imide and a urea. For example, N,N-dimethyl-α,α-dichlorobenzylamine can be obtained by chlorination of the carbonyl portion of the amide in N,N-dimethylbenzamide with phosgene or oxalyl chloride.

Examples of the amide include formylpiperidine, formylpiperazine, formylmorpholine, N,N-dimethylformamide, N,N-diethylformamide, N,N-di(n-propyl)formamide, N,N-diisopropylformamide, N,N-di(n-butyl)formamide, N,N-dipentylformamide, N,N-dimethylacetamide, N,N-diethylacetamide, N,N-dimethylpropionamide, N,N-dimthyltrifluoroacetamide, N,N-dimethylcyanoformamide, N,N-dimethylcyclopropanecarboxyamide, N,N-dimethyl-2-thiooxamide, N,N-dimethylbenzeneacetamide, N,N-dimethylacetoacetamide, N,N-dimethyl-2,2-dichloroacetoacetamide, N,N-dimethylphenoxyacetamide, N,N-diethyl-propionamide, N,N-diethylbutyramide, N,N-dimethylamide, N,N-dipropyl-acetamide, N,N-bis(2-hydroxymethyl)dodecanamide, N,N-dimethyl-aminoethyl-methacrylamide, N,N-diethyl-2-(1-naphthyloxy)propanamide, N,N-dibutylacetamide, 1-triphenylphosphoranyliden-2-propanone, N,N-diethyldecalylamide, N-methylformamide, N-methylacetamide, N,N-dimethylphenoxyacetamide, N,N-methyl-N-phenylformamide, N,N-dimethylbutyramide, N,N-dimethylisobutyramide, N,N-diethylisobutyramide, N,N-dimethylvaleramide, N,N-dimethylbenzamide, N,N-diethylmetatoluamide, N,N-diethyl-o-tolylamide, N,N-diethyl-p-tolylamide, N,N-diethyl(2,4-dimethyl)benzamide, N,N-diethyl(2,5-dimethyl)benzamide, N,N-diethyl(2,6-dimethyl)benzamide, N,N-diethyl(3,4-dimethyl)benzamide, N,N-diethyl(3,5-dimethyl)benzamide, N,N-diethyl(2,4,5-trimethyl)benzamide, N,N-diethyl(2,4,6-trimethyl)benzamide, N,N-dimethylaminoethylmethacrylamide, N,N-dimethylcinnamamide, N,N-dimethylfuran-2-carboxyamide, N,N-dimethylfuran-3-carboxyamide, N,N-diethyl(2-methoxy)benzamide, N,N-dimethyl-p-chlorobenzamide, N,N-dimethyl-p-bromobenzamide, N,N-dimethyl-p-fluorobenzamide, N,N-diethylmesitylamide, N,N-diethylnaphthylamide, N,N-diethylbiphenylamide, N,N-diethylanthrylamide, N,N-diethylcyclohexylamide, N,N-dimethyldecanamide, N,N-dimethyl-2-pyridinecarboxyamide, benzoylpiperidine, benzoylmorpholine, dimethylurea, diethylurea, diphenylurea, di(methylphenyl)urea, di(ethylphenyl)urea, 1,3-dimethylimidazolidin-2-one, 1-methylpiperidin-2-one and 1,3-dimethyltetrahydropyrimidin-2(1H)-one.

The above amides can be easily derived by the reaction of various types of amines with a carboxylic acid having the corresponding structure such as benzoic acid, isomers of methylbenzoic acid having the substituent at various positions, 4-ethylbenzoic acid, 4-n-propylbenzoic acid, 4-isopropylbenzoic acid, 4-n-butylbenzoic acid, 4-t-butylbenzoic acid, 4-isobutylbenzoic acid, isomers of methoxybenzoic acid having the substituent at various positions, 2,4-dimethylbenzoic acid, 2,5-dimethylbenzoic acid, 3,4-dimethylbenzoic acid, 3,5-dimethylbenzoic acid, 2,4,5-trimethylbenzoic acid, 2,4,6-trimethylbenzoic acid, 4-methylbiphenylcarboxylic acid, 4-ethylbiphenylcarboxylic acid, 4-n-propyl-biphenylcarboxylic acid and 4-n-butylbiphenylcarboxylic acid. Therefore, it is preferable that a carboxylic acid industrially easily available is selected as the starting material.

Specifically, for example, 3-methylbenzoic acid and diethylamine can be converted into N,N-diethyl-3-methylbenzamide.

The α,α-dihaloamine represented by general formula (2) can be obtained by introducing a halogen into the amide described above. A halogenating agent can be used for the introduction. For introducing chlorine, for example, oxygen atom of the amide bond is replaced with chorine atom by using a chlorinating agent such as phosgene, oxalyl chloride, thionyl chloride, phosphorus trichloride and phosphorus pentachloride, as heretofore well known. In general, the halogenation of a carboxylic acid amide proceeds easily. In the case of isobutyramide, the reaction is completed in a short time by the chlorination in dichloromethane under a stream of phosgene at 20° C. (refer to Organic Synthesis, CV 6, 282).

When the reactivity of chlorine is small, a halogen having a greater reactivity can be selected from analogous halogens including bromine and iodine. A halogen can be introduced into other amides under a similar condition.

The Lewis base used in the present invention is not particularly limited. Preferable examples of the Lewis base include triethylamine, n-butylamine, pyridine, quinoline, melamine, γ-cholidine, piperidine, piperazine and morpholine. Among these Lewis bases, triethylamine is preferable from the standpoint of the reactivity and the easiness of handling.

In the present invention, in the halogen-fluorine exchange reaction using the α,α-dihaloamine represented by general formula (2) as the substrate, HF and the Lewis base of the reactants are used each in an amount by mole in the range of 90 to 110% based on the amount by mole of the halogen atom represented by X in the α,α-dihaloamine.

When the amount of HF in the reaction system exceeds the stoichiometric amount, a portion of HF is left remaining after the reaction is completed. The residual HF may exhibit adverse effects, and there is the possibility that the halogen-fluorine exchange reaction is adversely affected or the formed product cannot be separated due to the strong interaction between HF and the nitrogen atom. When the amounts by mole of HF and the Lewis base is within the above range, fluorine is substantially completely consumed to form the object product. The hydrogen halide formed in combination with the α,α-difluoroamine of the object compound is converted into a salt with the Lewis base which can be removed to the outside of the system easily.

Although it is most preferable that the amounts by mole of HF and the Lewis base in the system are each the same as the amount by mole of the halogen atom represented by X in the substrate, no problems arise actually as long as the amounts are each in the range of 90 to 110% by mole.

Although HF and the Lewis base may be introduced into the system separately in each prescribed amount, it is preferable that a molecular compound of HF and the Lewis base (HF-Lewis base) is used instead of using HF which causes severe corrosion and difficulty in handling.

In HF-Lewis base, i.e., the molecular compound comprising HF and the Lewis base, the relative amounts of HF and the Lewis base are not always 1:1. When a molecular compound of triethylamine and HF in relative amounts by mole of 1:n is expressed as $Et_3N$-$nHF$ (n representing an integer of 1 or greater), examples of the molecular compound include $Et_3N$-$1HF$, $Et_3N$-$2HF$, $Et_3N$-$3HF$, $Et_3N$-$4HF$, $Et_3N$-$5HF$ and $Et_3N$-$6HF$. Among these compounds, $Et_3N$-$3HF$ which has little possibility of causing corrosion, can be distilled and can be handled safely is preferable.

When the molecular compound in which the relative amounts by mole of the Lewis base and HF are 1:1 is used as HF-Lewis base, the amounts by mole of HF and the Lewis base are each adjusted at 90 to 110% based on the amount by mole of the halogen atom represented by X in the substrate by introducing $Et_3N$-$1HF$ in an amount by mole of 90 to 110% based on the amount by mole of the halogen atom represented by X in the substrate.

On the other hand, when a molecular compound having 2 moles or more of HF per one mole of the Lewis base such as $Et_3N$-$2HF$ and $Et_3N$-$3HF$ is used, the amount by mole of the Lewis base (triethylamine) is not adjusted at 90 to 110% based on the amount by mole of the halogen atom represented by X in the substrate by introducing $Et_3N$-$3HF$ in an amount such that the amount by mole of HF is 90 to 110% based on the amount by mole of the halogen atom represented by X in the substrate. Therefore, a supplemental amount of the Lewis base (triethylamine) is introduced so that the above condition is satisfied. More specifically, the case in which N,N-diethyl-α-chlorometatoluoylamidium chloride having 2 chlorine atoms to be exchanged with fluorine atoms is used as the substrate and $Et_3N$-$3HF$ is used as HF-Lewis base will be described. When ⅔ moles of $Et_3N$-$3HF$ is added per 1 mole of the substrate (2 moles of chlorine atom) and, then, 4/3 moles of triethylamine is added immediately thereafter or after some time, the amounts by mole of HF and triethylamine in the system each become the same as the amount by mole of chlorine atom to be exchanged.

Although the halogen-fluorine exchange reaction in the present invention may be conducted without solvents, it is preferable that the substrate, HF and the Lewis base are dissolved or dispersed in a solvent.

As the solvent used for the reaction, aliphatic hydrocarbons, aromatic hydrocarbons, halogenated hydrocarbons, aromatic halogenated hydrocarbons, nitrites, ethers and carboxylic acid amides having the structure of the raw material used for producing the α,α-dihaloamine of the substrate, which are inert to the substrate, HF, the Lewis base and the product, are preferable. Among these solvents, halogenated hydrocarbons such as methyl chloride, dichloromethane, chloroform and carbon tetrachloride and aliphatic nitriles such as acetonitrile are preferable, and dichloromethane is more preferable. The solvent for the reaction may be used singly or in combination of two or more. It is preferable that the solvent for the reaction is used in an amount by mass, in general, 1 to 30 times and preferably 2 to 10 times the amount by mass of the substrate.

The halogen-fluorine exchange reaction can be conducted in accordance with a batch process, a semibatch process or a continuous process and in accordance with an ordinary thermal process or a process under irradiation with microwaves. It is preferable that the reaction is conducted at a temperature of 100° C. or lower and more preferably at a temperature in the range of 0 to 60° C. In general, the reaction is conducted at the room temperature. The reaction may be conducted at a temperature of 0° C. or lower. The reaction time for the exchange reaction is preferably 10 hours or less, and more preferably from 10 minutes to 4 hours.

When the halogen-fluorine exchange reaction is completed, a salt of the hydrogen halide and the Lewis base in the same amounts by mole is formed. The spontaneously formed salt or the salt formed after removal of the solvent by distillation is separated by filtration. It is not always necessary that the solvent is completely removed by the distillation. After a suitable amount of the solvent is removed, a poor solvent to the salt of the hydrogen halide and the Lewis base such as hexane and heptane is added to form the salt, then separate the salt by filtration. The crude product obtained after the filtration is purified by distillation or by extraction with a solvent, and the α,α-difluoroamine of the object compound can be obtained with a great purity.

When water is present in the system, the crude product frequently becomes a slurry containing an amide formed by hydrolysis. In this case, it is preferable that the product is treated by extraction with an aliphatic hydrocarbon, an aromatic hydrocarbon, a halogenated hydrocarbon, an aromatic halogenated hydrocarbon, a nitrile or an ether, which is inert to the product. Specifically, when N,N-diethyl(3-methyl)benzamide is chlorinated, and N,N-diethyl-α,α-difluoro(3-methyl)benzylamine is produced in accordance with the halogen-fluorine exchange reaction using $Et_3N$-$3HF$, it is preferable that an aliphatic hydrocarbon such as n-hexane and n-heptane is used as the solvent for the extraction. The α,α-difluoroamine of the object compound can be obtained by removing the solvent of the extraction by distillation. Further purifications such as distillation may be conducted to obtain the product having a greater purity.

Examples of the industrial application of the present invention include processes comprising steps of halogenating a carboxylic acid amide of the starting material, conducting the halogen-fluorine exchange reaction after or without separation of the obtained halogenated product, separating the object product by filtration after the reaction has been completed and purifying the separated product.

EXAMPLES

The present invention will be described more specifically with reference to examples in the following. However, the present invention is not limited to the examples.

Example 1

Preparation of N,N-diethyl-α,α-difluoro(3-methyl)benzylamine

A three-necked flask (200 ml) used as the reactor was kept at the room temperature under the atmosphere of nitrogen. After 50 ml of dichloromethane was poured into the flask, 9.56 g (0.050 moles) of N,N-diethylmetatoluamide and 6.8 g (0.0536 moles) of oxalyl chloride were added under stirring. After 30 minutes, the resultant mixture was kept under the refluxing temperature (47° C.) for 90 minutes to chlorinate N,N-diethylmetatoluamide, and N,N-diethyl-α,α-dichloro (3-methyl)-benzylamine was obtained. When generation of gas ended, 5.7 g (0.0354 moles) of triethylamine-3HF was added dropwise while the reactor was cooled with ice and, then, 7.3 g (0.0721 moles) of triethylamine was added dropwise in the same manner. When the addition was completed, the reactor was dipped into a water bath kept at 20° C., and the chlorine-fluorine exchange reaction was allowed to proceed for 30 minutes. During the reaction, generation of gas and formation of a white solid substance were observed.

When the chlorine-fluorine exchange reaction was completed, the formed solid substance was removed by filtration, and dichloromethane of the solvent was removed by distillation. The product was extracted by adding 20 ml of n-hexane three times to the residue obtained after the removal of the solvent by distillation. The extract was filtered to remove insoluble substances, and n-hexane was removed by distillation. The residue was further distilled under a reduced pressure, and 8.54 g of N,N-diethyl-α,α-difluoro(3-methyl)benzylamine was obtained as a colorless fraction at 55 to 57° C. under a pressure of 4 mmHg. The yield was 80% based on the amount of N,N-diethylmetatoluamide.

Comparative Example 1

Preparation of N,N-diethyl-α,α-difluoro(3-methyl)benzylamine a) Preparation of N,N-diethyl-α-chlorometatoluoylamidium Chloride Under the atmosphere of nitrogen, 125 g of a carbon tetrachloride solution containing 25 g (0.197 moles) of oxalyl chloride was placed into a three-necked flask (500 ml). Under cooling with ice, 45 g (0.236 moles) of N,N-diethylmetatoluamide was added dropwise over 20 minutes under stirring. The resultant mixture was kept being stirred for 10 minutes after the addition was completed. Then, the mixture was kept at 50° C. for 1 hour so that N,N-diethylmetatoluamide was chlorinated. During the reaction, a white solid substance was formed, and gas was generated. The formed solid substance was separated by filtration, washed with carbon tetrachloride and n-hexane and then dried, and 47.5 g (the yield: 98%) of N,N-diethyl-α-chlorometatoluoylamidium chloride was obtained.

b) Preparation of N,N-diethyl-α,α-difluoro(3-methyl)benzylamine

In a glove box kept under the atmosphere of nitrogen, 250 g of acetonitrile, 25 g (0.1 mole) of N,N-diethyl-α-chlorometatoluoylamidium chloride obtained above in a) and 23.5 g (0.4 moles) of KF (manufactured by MORITA KAGAKU Co., Ltd.; a product in accordance with the spray drying process) were placed into a three-necked flask (500 ml), and the chlorine-fluorine exchange reaction was allowed to proceed at the refluxing temperature of acetonitrile (74° C.) for 18 hours. Then, the reaction mixture was cooled at the room temperature and filtered. The filtrate was concentrated under a reduced pressure using an evaporator and distilled in the same manner as that conducted in Example 1, and 13 g (the yield: 60%) of N,N-diethyl-oα,α-difluoro(3-methyl)benzylamine was obtained.

Example 2

Preparation of N,N-diethyl-α,α-difluoro(3-methyl)benzylamine

Into a three-necked flask (500 ml), 100 ml of dichloromethane and 19.2 g (0.10 mole) of N,N-diethylmetatoluamide were placed and kept under the atmosphere of nitrogen. Then, 10.4 g (0.105 moles) of phosgene was introduced into the reactor at the room temperature over 30 minutes. Then, the chlorination was allowed to proceed at the refluxing temperature of dichloromethane (47° C.) for 90 minutes, and N,N-diethyl-α,α-dichloro(3-methyl)benzylamine was obtained. When generation of gas ended, 11.4 g (0.072 moles) of Et$_3$N-3HF was added dropwise under cooling with ice. Then, 14.6 g (0.145 moles) of triethylamine was added dropwise in the same manner, and the reactor was dipped into a water bath at 20° C. and kept there for 30 minutes. The formed solid substance was removed, and dichloromethane of the solvent was removed by distillation under a reduced pressure. The product was extracted by adding 20 ml of n-hexane three times to the residue obtained after the removal of the solvent. The extract was filtered to remove insoluble substances, and n-hexane was removed by distillation. The residue was further distilled under a reduced pressure, and, 17.1 g (the yield: 81%) of N,N-diethyl-α,α-difluoro(3-methyl)benzylamine was obtained as a colorless fraction at 55 to 57° C. under a pressure 4 mmHg.

Example 3

Preparation of N,N-diethyl-α,α-difluoro(2-methoxy)benzylamine a) Preparation of N,N-diethyl-α-chloro(2-methoxy)phenylamidium Chloride Under the atmosphere of nitrogen, a 45% carbon tetrachloride solution of oxalyl chloride (oxalyl chloride: 24.5 g, 0.193 moles) was placed into a four-necked flask (200 ml). While the atmosphere of nitrogen was maintained under a slightly added pressure, 20.05 g (0.0965 moles) of o-methoxy-N,N-diethylbenzamide was added dropwise at the room temperature (an increase in the temperature at the inside of 5° C.).

When the addition was completed, the resultant mixture was kept at 53° C. for 5 hours. The reaction fluid showed separation into two layers. The reaction was terminated by lowering the temperature at the room temperature, and the solvent was removed by distillation to obtain a viscous liquid substance. When the viscous liquid substance was left standing in a glove box, a brown solid substance was separated from the viscous liquid (the amount of the solid substance: 26.6 g). The obtained solid substance was washed with n-hexane and carbon tetrachloride and dried, and 21.4 g (the yield: 80%) of N,N-diethyl-α-chloro(2-methoxy)-phenylamidium chloride was obtained.

b) Preparation of N,N-diethyl-α,α-difluoro(2-methoxy)benzylamine

In a glove box kept under the atmosphere of nitrogen, 13.8 g (0.050 moles) of N,N-diethyl-α-chloro(2-methoxy)phenylamidium chloride obtained as described above in a) and 5.7 g (0.0359 moles) of $Et_3N$-3HF were placed dropwise into a three-necked flask (200 ml). Then, 7.3 g (0.0723 moles) of triethylamine was added dropwise in the same manner. When the addition was completed, the reactor was dipped into a water bath at 20° C. and kept there for 30 minutes. When the reaction was completed, the formed solid substance was separated by filtration, and dichloromethane of the solvent was removed by distillation. The product was extracted by adding 20 ml of n-hexane three times to the residue obtained after the removal of the solvent by distillation. After the extract was filtered to remove insoluble substances, n-hexane was removed by distillation, and 8.4 g (the yield: 76%) of N,N-diethyl-α,α-difluoro-(2-methoxy)benzylamine was obtained.

Comparative Example 2

Procedures similar to those conducted in Example 2 were conducted. A four-necked flask equipped with a magnetic stirrer and a reflux condenser was used as the reactor. Into the reactor, 50 g of acetonitrile, 5.0 g (0.0181 moles) of N,N-diethyl-α-chloro(2-methoxy)phenylamidium chloride and 4.43 g (0.076 moles) of KF prepared in accordance with the spray drying process were placed, and the chlorine-fluorine exchange reaction was allowed to proceed under the atmosphere of nitrogen of a slightly added pressure at 600 rpm at 80° C. for 20 hours. After the reaction was terminated by lowering the temperature to the room temperature, the reaction fluid was filtered and washed. Then, acetonitrile of the solvent was removed by distillation, and 3.51 g (the yield: 67%) of N,N-diethyl-α,α-difluoro(2-methoxy)benzylamine was obtained.

Example 4

Preparation of 2,2-difluoro-1,3-dimethylimidazolidine

The same procedures as those conducted in Example 3b) were conducted except that 8.45 g (0.05 moles) of 2-chloro-1,3-dimethylimidazolidinium chloride was used as the substrate, and 6.2 g (the yield of isolation: 91%) of 2,2-difluoro-1,3-dimethylimidazolidine of the object compound was obtained.

Comparative Example 3

In a glove box kept under the atmosphere of nitrogen, 15 g (0.13 moles) of 1,3-dimethyl-2-imidazolidinone, 8.45 g (0.5 moles) of 2-chloro-1,3-dimethylimidazolidinium chloride and 11.62 g (0.2 moles) of KF prepared in accordance with the spray drying process were placed into a three-necked flask (200 ml). Then, the flask was kept at 85° C. for 24 hours, and the chlorine-fluorine exchange reaction was allowed to proceed. As the result of analysis of the reaction fluid in accordance with the high performance liquid chromatography (HPLC), it was found that the yield did not exceed 96%, and the reaction was not completed even through it took a long time for the reaction. Inorganic salts were separated from the reaction fluid by filtration, and the obtained inorganic salts were washed with 10 ml of 1,3-dimethyl-2-imidazolidinone twice. The filtrate and the washing liquids were combined and distilled under a reduced pressure, and 6.85 g (the yield of isolation: 81%) of 2,2-difluoro-1,3-dimethylimidazolidine was obtained.

Example 5

The same procedures as those conducted in Example 1 were conducted except that 5.66 g (0.050 moles) of piperidin-1-carbaldehyde (formylpiperidine) was used in place of N,N-diethylmetatoluamide, and 5.58 g (the yield of isolation: 82%) of 1-(difluoromethyl)piperidine was obtained.

Then, the product was analyzed by the measurements of the nuclear magnetic resonance (NMR). The measurement of $^1$H-NMR was conducted in heavy chloroform as the solvent using JMN-EX270 (270 MHz) manufactured by NIPPON DENSHI Co., Ltd. The measurements of $^{13}$C-NMR and $^{19}$F-NMR were conducted in heavy chloroform as the solvent using NMR-LA500SS (500 MHz) manufactured by NIPPON DENSHI Co., Ltd. The results of the measurements of NMR are shown in the following:

$^1$H-NMR: δ value (ppm), TMS as the reference, measured in $CDCl_3$
2.81 (m, 4H, —$CH_2$—N-×2)
1.55 (m, 6H, —$CH_2$—$CH_2$—$CH_2$—N—, —$CH_2$—$CH_2$—$CH_2$—N-×2)
5.90 (s, 1H, —$CF_2$—H)

$^{13}$C-NMR: δ value (ppm), TMS as the reference, at −50° C., measured in $CDCl_3$
24.12 (s, —$CH_2$—$CH_2$—N-×2)
24.76 (s, —$CH_2$—$CH_2$—$CH_2$—N—)
44.38 (s, —$CH_2$—N-×2)
117.66 (t, 246 Hz, —$CF_2$)

$^{19}$F-NMR: δ value (ppm), $CF_3COOH$ as the reference, at −50° C., measured in $CDCl_3$
−101.10 (d, 2F, J=69.13)

Example 6

The same procedures as those conducted in Example 1 were conducted except that 5.76 g (0.050 moles) of morpholin-4-carbaldehyde (formylmorpholine) was used in place of N,N-diethylmetatoluamide, and 5.49 g (the yield of isolation: 80%) of 4-(difluoromethyl)morpholine was obtained.

Then, the product was analyzed by the measurements of NMR under the same conditions as those in Example 5. The results of the measurements of NMR are shown in the following:

$^1$H-NMR: δ value (ppm), TMS as the reference, measured in $CDCl_3$
2.85 (t, 4H, J=4.86, —$CH_2$—N-×2)
3.71 (t, 4H, J=4.86, —O—$CH_2$-×2)
5.93 (s, 1H, —$CF_2$—H)

$^{13}$C-NMR: δ value (ppm), TMS as the reference, at −50° C., measured in $CDCl_3$ 43.46 (s, —CH$_2$—N-×2)
66.00 (s, —O—CH$_2$-×2)
116.78 (t, 244 Hz, —CF$_2$)
$^{19}$F-NMR: δ value (ppm), CF$_3$COOH as the reference, at −50° C., measured in CDCl$_3$
−102.95 (d, 2F, J=57.56, =CF$_2$)

As shown in Most Preferred Embodiment to Carry Out the Invention and Examples, it frequently takes a long time to complete the halogen-fluorine exchange reaction in accordance with the conventional process using an inorganic salt such as KF. In contrast, in accordance with the present invention, the reaction can be rapidly completed in a short time. HF can be almost completely converted into the α,α-difluoroamine and the salt of the Lewis base and the hydrogen halide when the relative amounts by mole of HF and the Lewis base in the reaction system are adjusted within the specific range described above based on the amount by mole of the halogen atom in the substrate. The α,α-difluoroamine of the object product can be easily separated by removing the salt by filtration, and the production process which can be conducted easily with excellent productivity can be constructed. In particular, when the reaction is conducted using HF-Lewis base, the process is advantageous in that handling is easy and no special apparatuses or technologies are required since corrosion is absent unlike HF.

INDUSTRIAL APPLICABILITY

The process of the present invention is an excellent process which can produce α,α-difluoroamines useful as the nucleophilic fluorinating agent in a short time with a great yield, is economical and can be industrially applied. In particular, when HF is introduced into the reaction system in the form of a molecular compound with a Lewis base in the present invention, the process is industrially advantageous since handling is easy and no special apparatuses or technologies are required due to the absence of corrosion.

The invention claimed is:

1. A process for producing an α,α-difluoroamine represented by general formula (1) in accordance with a halogen-fluorine exchange reaction using an α,α-dihaloamine represented by general formula (2) as a substrate, wherein hydrogen fluoride and a Lewis base are used for the exchange reaction each in an amount by mole in a range of 90 to 110% based on an amount by mole of a halogen atom represented by X in the α,α-dihaloamine, and a salt of a hydrogen halide and the Lewis base formed by the exchange reaction is removed to outside of a reaction system:

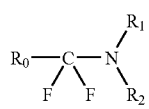

(1)

wherein R$_0$, R$_1$ and R$_2$ each represent hydrogen atom or an alkyl group, an aryl group, an alkylamino group or an arylamino group, which may have substituents, atoms and groups represented by R$_0$, R$_1$ and R$_2$ may be same with or different from each other, and a ring may be formed by bonding of two or more groups represented by R$_0$, R$_1$ and R$_2$;

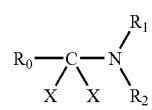

(2)

wherein R$_0$, R$_1$ and R$_2$ each represent hydrogen atom or an alkyl group, an aryl group, an alkylamino group or an arylamino group, which may have substituents, atoms and groups represented by R$_0$, R$_1$ and R$_2$ may be same with or different from each other, a ring may be formed by bonding of two or more groups represented by R$_0$, R$_1$ and R$_2$, and X represents chlorine atom, bromine atom or iodine atom.

2. A process for producing α,α-difluoroamine according to claim 1, wherein hydrogen fluoride and the Lewis base are introduced into the reaction system as a molecular compound of hydrogen fluoride and the Lewis base or a combination of the Lewis base and a molecular compound of hydrogen fluoride and the Lewis base.

3. A process for producing an α,α-difluoroamine according to claim 1, wherein the Lewis base is triethylamine, n-butylamine, pyridine, quinoline, melamine, γ-cholidine, piperidine, piperazine or morpholine.

4. A process for producing an α,α-difluoroamine according to claim 2, wherein the molecular compound of hydrogen fluoride and the Lewis base is triethylamine-3HF.

5. A process for producing an α,α-difluoroamine according to claim 1, wherein X in general formula (2) represents chlorine atom.

6. A process for producing an α,α-difluoroamine according to claim 1, wherein, in general formula (1) and general formula (2), R$_0$ represents phenyl group, 2-methylphenyl group, 3-methylphenyl group, 4-methylphenyl group, 4-ethylphenyl group, 4-n-propylphenyl group, 4-isopropylphenyl group, 4-n-butylphenyl group, 4-t-butylphenyl group, 4-isobutylphenyl group, 2-methoxyphenyl group, 3-methoxyphenyl group, 4-methoxyphenyl group, 2,4-dimethylphenyl group, 2,5-dimethylphenyl group, 3,4-dimethylphenyl group, 3,5-dimethylphenyl group, 2,4,5-trimethylphenyl group, 2,4,6-trimethylphenyl group, 4-methylbiphenyl group, 4-ethylbiphenyl group, 4-n-propylbiphenyl group or 4-n-butylbiphenyl group, and R$_1$ and R$_2$ each represent an alkyl group or an aryl group each having 16 or less carbon atoms.

* * * * *